(12) United States Patent
Newkome et al.

(10) Patent No.: US 8,841,451 B2
(45) Date of Patent: Sep. 23, 2014

(54) METHODS OF NANOASSEMBLY OF A FRACTAL POLYMER AND MATERIALS FORMED THEREBY

(75) Inventors: George R. Newkome, Medina, OH (US); Charles N. Moorefield, Chagrin Falls, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/548,664

(22) Filed: Jul. 13, 2012

(65) Prior Publication Data

US 2013/0066078 A1     Mar. 14, 2013

Related U.S. Application Data

(63) Continuation of application No. 12/299,486, filed as application No. PCT/US2007/068657 on May 10, 2007, now Pat. No. 8,227,614.

(60) Provisional application No. 60/746,944, filed on May 10, 2006.

(51) Int. Cl.
   *C07D 401/14* (2006.01)
   *C07F 15/02* (2006.01)
   *C07F 15/00* (2006.01)

(52) U.S. Cl.
   CPC ........... *C07F 15/0053* (2013.01); *C07F 15/025* (2013.01)
   USPC .............................................. 546/2; 546/257

(58) Field of Classification Search
   None
   See application file for complete search history.

(56) References Cited

FOREIGN PATENT DOCUMENTS

WO     WO 0107497 A2 *  2/2001

OTHER PUBLICATIONS

Newkome, et al. Chem. Eur. J. 10:1493 (2004).*

* cited by examiner

*Primary Examiner* — Michael Barker
(74) *Attorney, Agent, or Firm* — Renner Kenner Greive Bobak Taylor & Weber

(57) ABSTRACT

The invention relates to the formation of synthesized fractal constructs and the methods of chemical self-assembly for the preparation of a non-dendritic, nano-scale, fractal constructs or molecules. More particularly, the invention relates to fractal constructs formed by molecular self-assembly, to create synthetic, nanometer-scale fractal shapes. In an embodiment, a nanoscale Sierpinski hexagonal gasket is formed. This non-dendritic, perfectly self-similar fractal macromolecule is comprised of bisterpyridine building blocks that are bound together by coordination to (36) Ru and (6) Fe ions to form a nearly planar array of increasingly larger hexagons around a hollow center.

26 Claims, 9 Drawing Sheets

METHODS OF NANOASSEMBLY OF A FRACTAL POLYMER AND MATERIALS FORMED THEREBY

CROSS-REFERENCE TO RELATED APPLICATIONS

This application is a continuation of U.S. patent application Ser. No. 12/299,486, filed Nov. 4, 2008, now U.S. Pat. No. 8,227,614, which claims priority to PCT Application No. PCT/US07/68657, filed May 10, 2007, which claims priority to Provisional U.S. Application No. 60/746,944, filed May 10, 2006.

STATEMENT REGARDING FEDERALLY SPONSORED RESEARCH OR DEVELOPMENT

This invention was made with U.S. government support under cooperative agreements by the National Science Foundation [DMR-0196231, DMR-0401780, CHE-0116041; CHE-0509989], the Air Force office of Scientific Research [F49620-02-1-0428, 02], and the Department of Energy [DE-FB02-02ER46012]. The U.S. government may have certain rights to the invention.

BACKGROUND OF THE INVENTION

Fractal constructs are based on the incorporation of identical motifs that repeat on differing size scales. Examples of fractal shapes in nature include clouds, trees, waves on a lake, the human circulatory system, and mountains, to mention but a few. The study of fractals has moved from the field of pure mathematics, to descriptions of nature that, in turn, inspired artistic design. More recently, chemists have incorporated the fractal form in molecular synthesis. Since 1985, molecular trees, which generally branch in a binary or ternary pattern, have been synthesized with increasing size and structural complexity. Beyond their aesthetics, these dendrimers and hyperbranched materials are now under study for a wide range of practical applications. However, tree-like patterns are but one type of fractal comprised of repeating geometrical figures. A porphyrin-based dendrimer that uses porphyrins as branching centers has been prepared that incorporates the snake-like "Kolam" fractal pattern described by Ascher for example. Nonetheless, most mathematically-defined fractals have yet to be produced in the laboratory.

It would therefore be beneficial to provide the chemical synthesis of fractal constructs, such as non-dendritic fractal constructs, based on Sierpinski's hexagonal gasket (incorporating both the Star of David and a Koch snowflake) where the terminology 'non-dendritic' refers to repeat units that do not branch in the typical tree-like pattern.

SUMMARY OF THE INVENTION

Based upon the foregoing, the present invention is directed to fractal constructs comprising, a first generation construct formed of a first predetermined molecular structure. A second generation construct is formed, such as by self-assembly, from a plurality of assembled first generation constructs, wherein the second generation construct possesses at least one architectural similarity to the first generation construct and having an interior surface area, and an exterior surface area. A third generation construct comprises a plurality of assembled second generation constructs, wherein the third generation construct possesses at least one architectural similarity and has an interior surface area and an exterior surface area. The third generation construct forms a fractal configuration by a discrete molecular structure. The fractal construct may be formed as a non-dendritic, fractal-based molecular construct, having predetermined characteristics for use in a variety of systems or devices.

The invention is also directed to methods to create fractal constructs, such as non-dendritic, fractal-based molecular constructs using directed and self-assembly type chemical syntheses. Non-dendritic, fractal-based materials are predicated on the creation of materials (e.g., macromolecules and composites) possessing at least one repeating architectural feature at differing size scales. The fractal concept can also be expanded to include similarity in physical properties at differing size scales. Examples of architectural similarities include but are not limited to trigonal, pentagonal, and hexagonal motifs. Whereas, examples of similarity in physical properties at differing size scales include but are not limited to electro- and photo-luminescence, oxidation and reduction potentials, catalytic activity, and porosity. Fractal materials construction techniques can include any of the following methods of molecular connectivity: covalent bonding, hydrogen-bonding, ionic attraction, and hydrophilic/lipophilic interactions. Any logical combination of these methods of connectivity can also be envisioned for the construction of 1-, 2-, or 3-dimensional materials or composites.

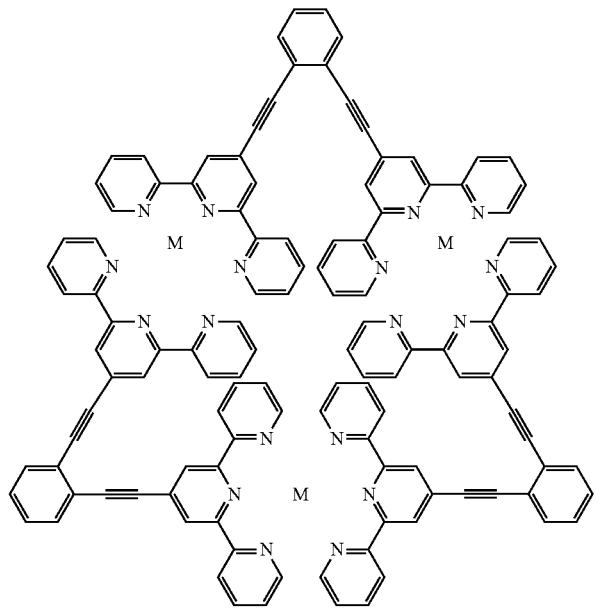

-continued

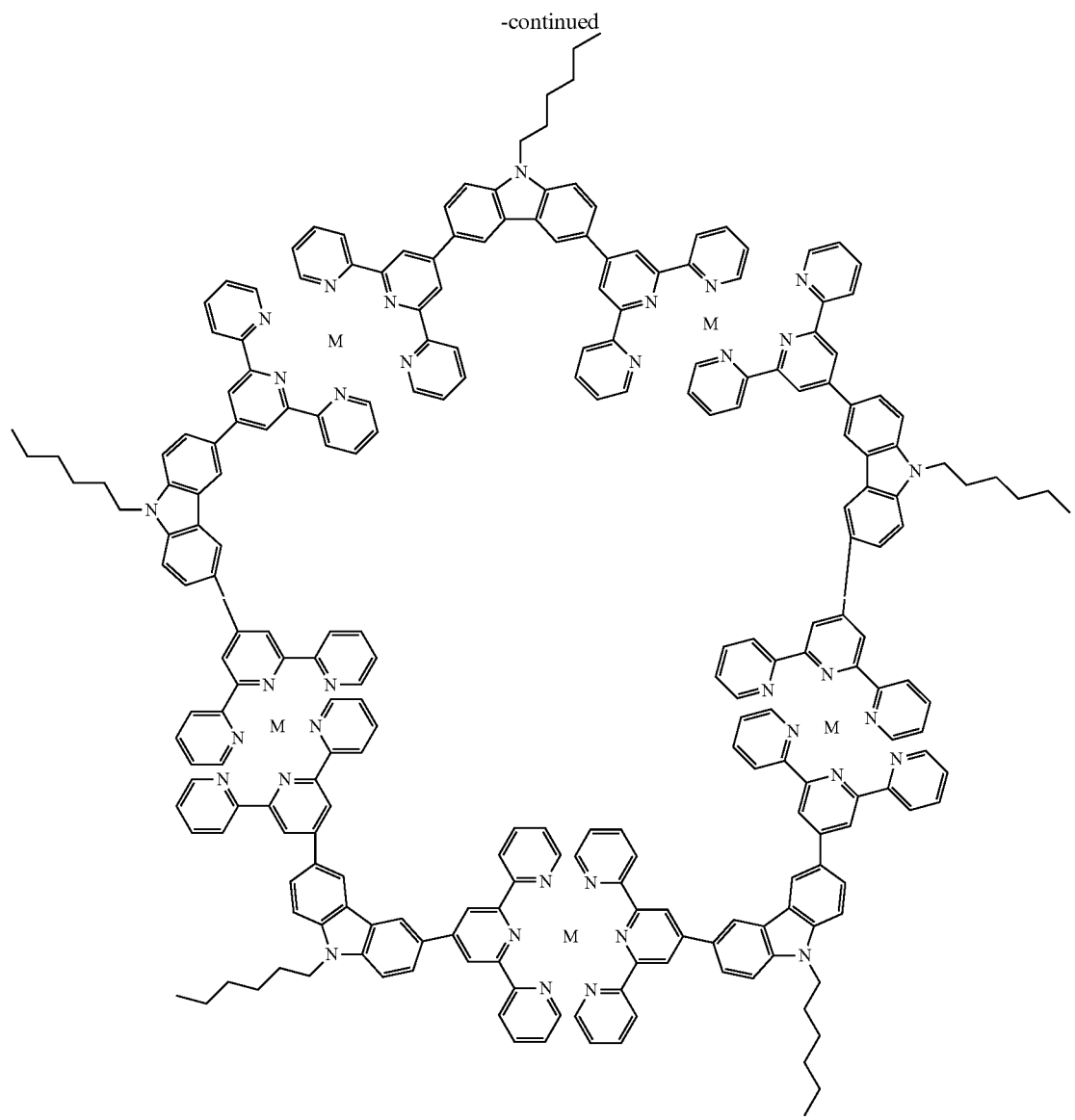

Where M = any 2+ metal, such as Ru(II), Fe(II), or Zn(II)

BRIEF DESCRIPTION OF THE DRAWINGS

FIG. 3B showing TEM pictures with 50 and 20 nm scale bars for the lower and higher resolution images, respectively (all image were obtained unstained); and FIG. 3C showing UHV-STM images (100×100 nm) on a Au(III) surface at 6 K revealing a line of gaskets settled on a ridge on the gold surface and a color enhanced and magnified image of a single molecule (scale bar=3 nm).

DESCRIPTION OF THE INVENTION

Figure 1A:
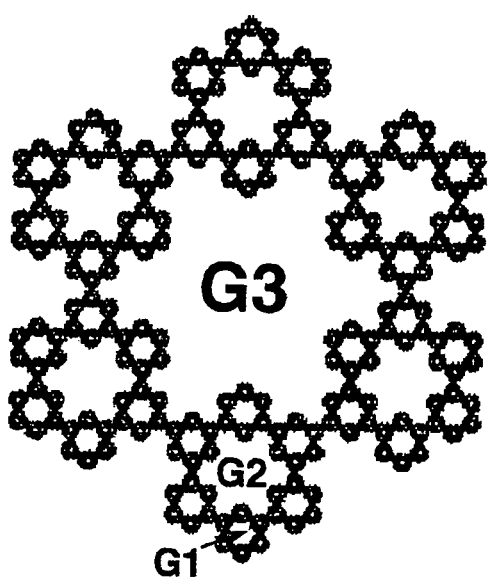
FIGS. 1A-1C is an example of a fractal construct according to the invention, showing generations G1-G3 relating to this example of a fractal-based construct. Images of the "Snake" kolam (B) and the 1→3 teaching pattern (C) of a tree.
Figure 1B:
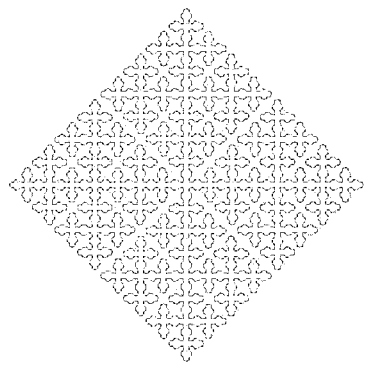
Figure 1C:
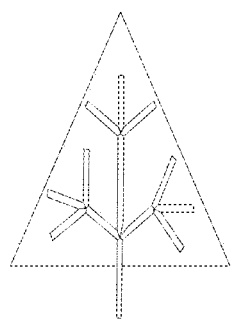

In an example of the invention, a fractal construct is formed to emulate a known fractal shape. The first mathematically-defined fractal was derived in 1915, when the Polish mathematician Vaclav Sierpinski described a series of interrelated equilateral triangles, later coined by Mandelbrot as the "Sierpinski Gasket". The original equation has been expanded, into other fractal constructs called Sierpinski "n-gons" including the hexagonal gasket. Mathematically, such fractal hexagonal structures result by operating on the points in a hexagon $H_0$ with six functions $$f_j(x, y) = \begin{bmatrix} 1/3 & 0 \\ 0 & 1/3 \end{bmatrix} \left( \begin{bmatrix} x \\ y \end{bmatrix} \right) + P_j,$$

$$J = 1, \ldots, 6$$

where $P_j$ are the vertices of $H_0$. Iteratively, this relations leads to: $H_{j+1}=f_1(H_j)+f_2(H_j)+f_3(H_j)+f_4(H_j)+f_5(H_j)+f_6(H_j)$, and the sequence $\{H_j\}$ converges to the hexagonal gasket shown in FIGS. 1A-1C. The mathematically-defined fractal pattern, the "Sierpinski hexagonal gasket", is formed according to an example, by means of chemical self-assembly, to form a fractal construct having a predetermined size and forming a complex discrete structure. Sierpinski's hexagonal gasket as shown in FIG. 1A incorporates the Star of David and the Koch Snowflake motifs, with G1-G3 indicating generations 1-3 that can be envisioned for this fractal-based construct. Images of the "Snake" kolam in FIG. 1B and 1→3 branching pattern shown in FIG. 1C of a tree.

Figure 2:
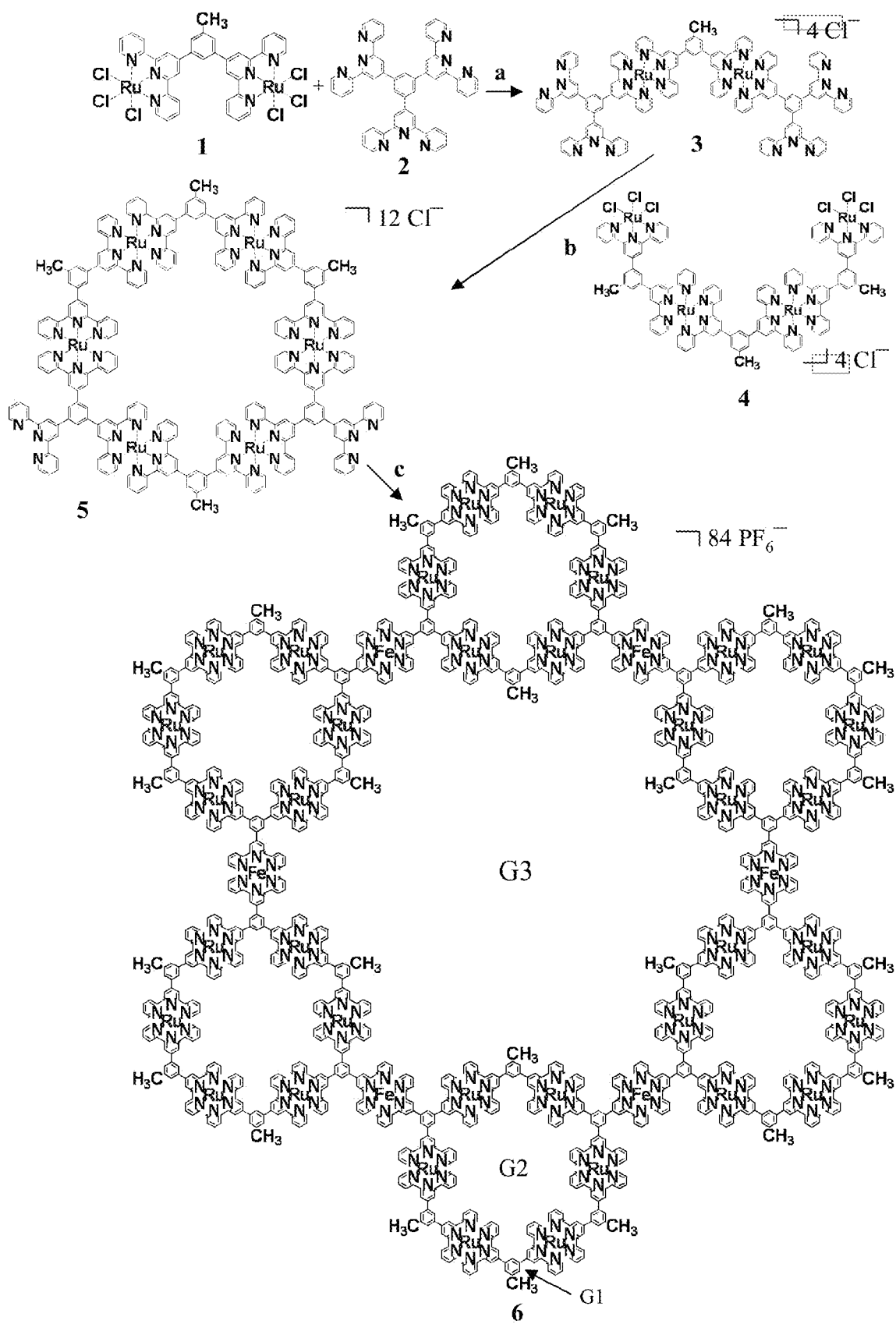
FIG. 2 shows the reaction scheme for the synthesis of the trimer of formula 3, the hexamer of formula 5, and the fractal gasket of formula 6. The representative hexagons that are noted constitute the generational growth of the fractal gasket.

To create the desired repeat unit, the invention in an embodiment utilizes 1 equivalent of bis-[Ru(III)] monomer as shown in FIG. 2. Turning to FIG. 2, the reaction scheme is shown for the synthesis of the trimer of formula 3, the hexamer of formula 5, and the fractal gasket of formula 6. Reaction conditions: a) compounds of formulas 1 and 2 were mixed with N-ethylmorpholine in refluxing $CH_3OH/CHCl_3$ (2:1 v/v), for 20 hours; b) compounds of formulas 3 and 4 were stirred in refluxing $Ch_3OH$ with added N-ethylmorpholine for 12 hours; c) 1. hexamer of formula 5 was refluxed in $Ch_3OH$ in the presence of one equivalent of $FeCl_2 \cdot 6H_2O$ for 20 hours, 2. To $CH_3OH$ solution of formula $5(Cl^-)_m(NO_3^-)_n$ was added a solution of $NH_4PF_6$ to obtain the desired gasket of formula 6 as a precipitate. The representative hexagons that are noted constitute the generational growth of the fractal gasket.

The monomer was heated with 4.5 equivalent of tristerpyridine as shown in FIG. 2 in refluxing $CHCl_3/CH_3OH$ for 20 hours under reducing conditions (added N-ethylmorpholine) to give the pivotal hetero-trimer as shown in FIG. 2 as deep red microcrystals in 35% yield. Its $^1H$ nuclear magnetic resonance (NMR) spectrum exhibited two singlets at 9.32 and 9.28 ppm in a 1:1 ratio, attributed to the four inner and outer 3',5'-tpyHs (where tpy=terpyridine) of the complexed ligands, as well as a resonance at 9.08 ppm assigned to the eight remaining 3',5'-tpyHs of the uncomplexed terpyridines, which integrated in a 2:1 ratio to the former downfield peaks; also, a singlet was observed at 2.89 ppm for the methyl groups. Electrospray ionization mass spectroscopy (ESI-MS) $[C_{139}H_{92}F_{24}N_{24}P_{12}Ru_2$ (2880.38): observed peaks at m/z: 2736.6 $(M-PF_6)^+$, 1295.9 $(M-2PF_6)^{2+}]$ gave further evidence for the desired structure. Following purification of the building blocks of formulae 3, 4, and 5 using a mixture of $H_2O$: $KNO_3$:$CH_3CN$, the counter ions were converted to $PF_6^-$ to facilitate a homogeneous ionic environment for ESI-MS analysis.

Treatment of the compound of formula 3 with homotrimer of formula 4 in the presence of N-ethylmorpholine produced the desired red microcrystalline hexamer of formula 5 in 31% yield; this structure was also confirmed by the ratio of the proton resonances (NMR) for the complexed and uncomplexed 3',5'-tpyHs. The EsI-MS (expected mass for the $C_{250}H_{170}F_{72}N_{42}P_{12}Ru_6$ cationic core and counter ions=6108.30) definitively showed the multiple-charged signals ranging from m/z at 1077.8 $(M-5PF_6)^{5+}$ to 364.2 $(M-12PF_6)^{12+}$ for the expected charge states. Treatment of hexamer 5 with one equivalent of $FeCl_2$ in refluxing $CH_3OH$ resulted in the one-step self-assembly of the desired fractal gasket 6, isolated in 35% yield, as a deep red solid. Column chromatography and dialysis removed the low molecular weight monomers as well as the linear, oligomeric materials. This material isolated as the polyCl$^-$ salt showed good solubility in $CH_3OH$, EtOH, DMF, and DMSO and poor solubility in $H_2O$, $CH_2Cl_2$, $CH_3CN$; whereas, following counter ion exchange to the polyPF$_6^-$ salt changes that trend to make them soluble in $CH_3CN$, DMF, and DMSO and insoluble in $CH_3OH$, EtOH, and $CH_2Cl_2$.

Although the fractal construct as describe din the previous example indicates the concepts of the invention, it should also be apparent that the invention is directed to methods to create various types and configurations of fractal constructs, such as non-dendritic, fractal-based molecular constructs, using directed and self-assembly type chemical syntheses. The non-dendritic, fractal-based materials in accordance with the invention are predicated on the creation of materials (e.g., macromolecules and composites) possessing at least one repeating architectural feature at differing size scales, which the previous example indicates. The fractal concept can also be expanded to include similarity in physical properties at differing size scales. Examples of architectural similarities include but are not limited to trigonal, pentagonal, and hexagonal motifs. Whereas, examples of similarity in physical properties at differing size scales include but are not limited to electro- and photo-luminescence, oxidation and reduction potentials, catalytic activity, and porosity. Fractal materials construction techniques can include any of the following methods of molecular connectivity: covalent bonding, hydrogen-bonding, ionic attraction, and hydrophilic/lipophilic interactions. Any logical combination of these methods of connectivity can also be envisioned for the construction of 1-, 2-, or 3-dimensional materials or composites. It is also possible to functionalize the formed fractal constructs for a variety of purposes or applications. For example, the constructs may be formed to have the propensity to stack with one another, or form other shapes when combined together in a predetermined fashion. Further, other functionalities can be incorporated for desired purposes or applications, such as providing the construct with predetermined characteristics, such as being lipophilic and/or hydrophilic at predetermined positions on or around the fractal construct. Any suitable materials for connecting the chemical building blocks of the generations of constructs are also contemplated. There is also the ability to precisely control the self-assembly of the fractal construct, thus making it possible to insert chemical component parts into the formed structure at precise locations, such as metals or other component parts. These precise locations are not limited to the association with other chemical constituents, but also relative to one another in space, as defined by the particular fractal construct. As further examples, the fractal constructs of the invention may be formed of other chemical building blocks, and may be formed in trigonal or pentagonal forms, such as follows:

7
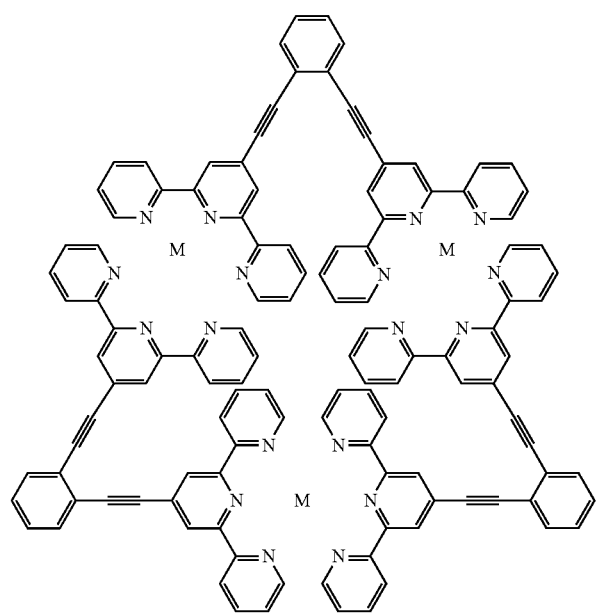
8
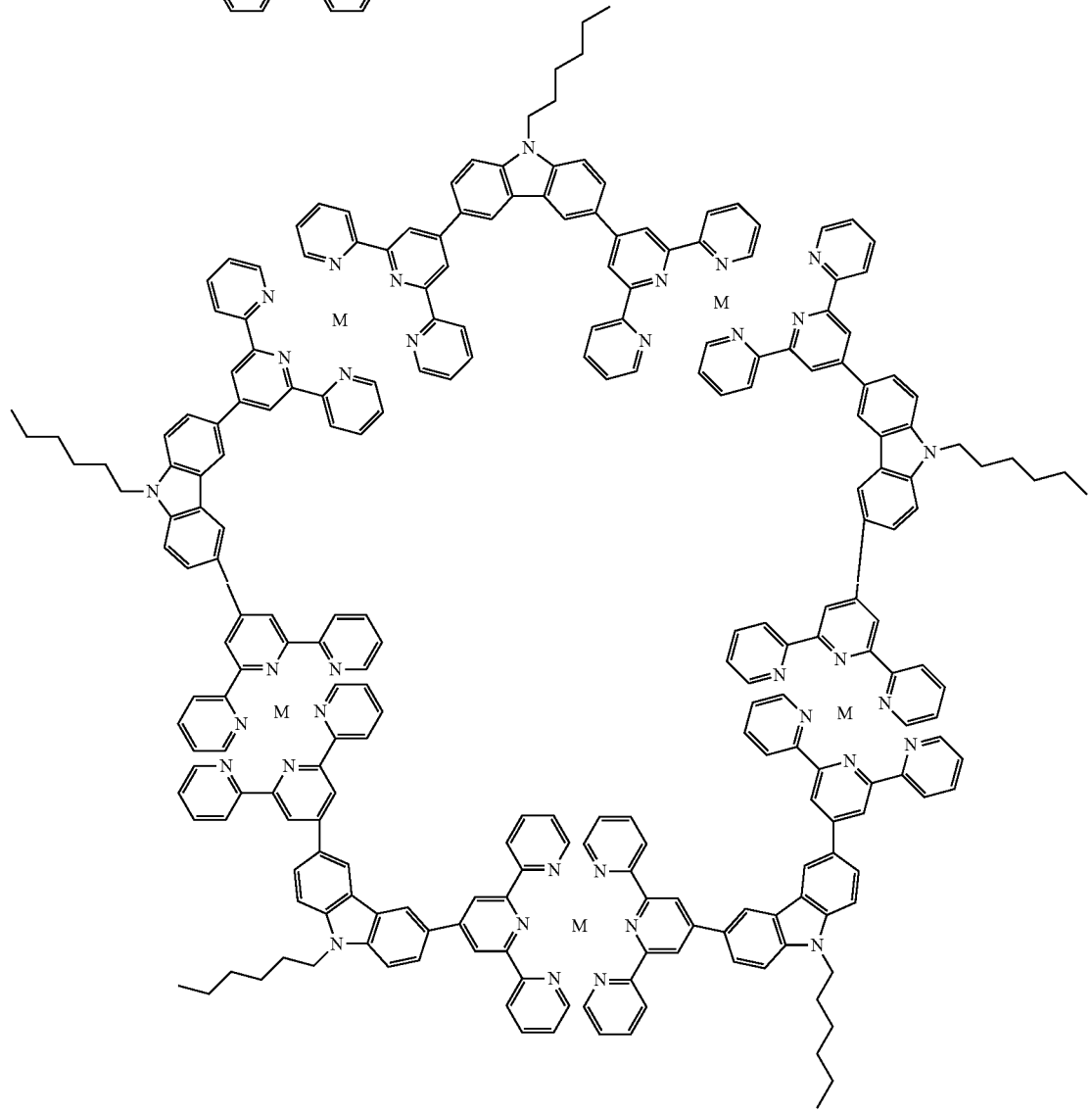
Where M = any 2+ metal, such as Ru(II), Fe(II), or Zn(II)

It should be apparent that the types of building blocks and shapes or architectural features can vary greatly, and all such possible constructions are contemplated. In the examples shown, the fractal constructs may be formed to provide functionalities such as for use in photovoltaics, molecular batteries or other such devices, or to form materials such as micelles or vesicles, for use in drug delivery techniques as an example. The fractal constructs may be formed to be hydrophobic and/or hydrophilic. For example, the fractal construct may have an outer surface area, such as in the second or third generation constructs, which is hydrophobic and the inner surface area is hydrophilic. Alternatively, the fractal construct could have the outer surface area hydrophilic and the inner surface area being hydrophobic. The fractal construct may also have photoluminescence properties, or other desired properties.

Again, it should be apparent that the ability to precisely form the fractal construct allows a wide variety of structures and functions to be provided.

Referring back to the example of gasket 6, the characterization of gasket 6 involved a considerable range of spectroscopic and electron microscopy techniques.

The use of a different metal in the last assembly step was planned, because different spectral properties using Fe(II) vs. Ru(II) connectivity would aid in the molecular characterization; notably, the all Ru(II) counterpart was easily formed by the use of [Ru(DMSO)$_4$Cl$_2$] in the final macrocyclization. In the case of the Fe—Ru construct, there should be a 1:6 Fe:Ru ratio observed for all macromolecules generated. Formation of the heterodinuclear construct was initially confirmed by $^1$H NMR measurements that showed two characteristic 3',5'-tpyH peaks one at 9.45 ppm attributed to the tpy-Fe-tpy complex and the other at 9.20 ppm attributed to the tpy-Ru-tpy complex, displaying the requisite 1:6 integration; a distinct singlet at 2.98 ppm for the methyl groups was also present. Ultraviolet visible (UV-vis) spectroscopy in CH$_3$CN (for PF$_6^-$) or CH$_3$OH (for Cl$^-$) showed the expected absorbance pattern at 575 and 495 nm with a 1:6 ratio for the tpy-Fe-tpy and tpy-Ru-tpy units, respectively. These results are consistent with that observed in a previous study where a hexagonal metallomacrocycle possessing 3 Fe and 3 Ru ions was prepared in an alternating pattern. As well, the individual (tpy)$_2$Fe and (CH$_3$C$_6$H$_4$tpy)$_2$Ru complexes were shown to have absorptions at 562 and 490, respectively; thus little or no cooperative effects can be attributed to the larger structures. Due to the overall 84$^+$ molecular charge, matrix-assisted laser desorption ionization time-of-flight mass spectroscopy (MALDI-TOF MS) measurements failed to provide definitive structural information, however, the ESI-MS spectrum showed a broad peak range from m/z at 310 to 970 attributed to the multi-charge stages m/z=35$^+$ to 84$^+$. Concerning bis(tpy)Ru(II)-based macrocycles, ESI-MS is superior to the MALDI technique because it has the advantages of direct detection of multiply charged ions, it does not change the complex connectivity through disassembly and reassembly processes, and it effects very little or no fragmentation.

Figure 8:
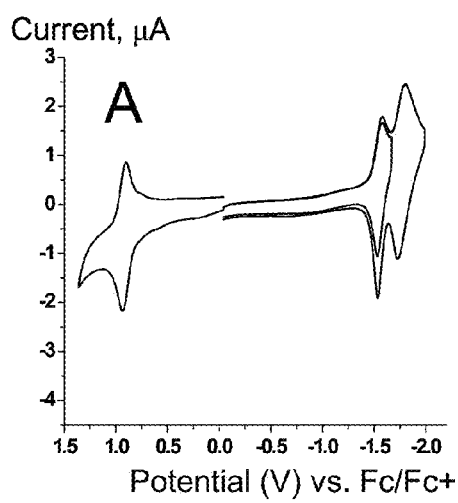
FIG. 8, shows in FIG. 8A the cyclic voltammogram of gasket 6 in $Ch_3CN$ (0.1 M $TBAPF_6$, scan rate 100 mV $sec^{-1}$), and in FIG. 8B a table of electrochemical potentials (mV vs $F_e/F_{e+}$, scan rate 100 mV $sec^{-1}$, $E_{pc}$=peak potential for the cathode, $E_{pa}$=peak potential for the anode, and $E_{pp}=E_{pc}-E_{pa}$).

The cyclic voltammogram (CV) of gasket 6 exhibits two reductive couples and one oxidative couple (FIG. 8). The first and second reductive couples are not reversible and the first has a sharp oxidative peak that grows with each successive scan due to adsorption on the electrode surface. The third redox couple observed around 1 V corresponds to the oxidation of Ru(II); however, the oxidation potential of Fe(II) is very close to this value. The data are entirely consistent with the proposed structure.

Figure 4:
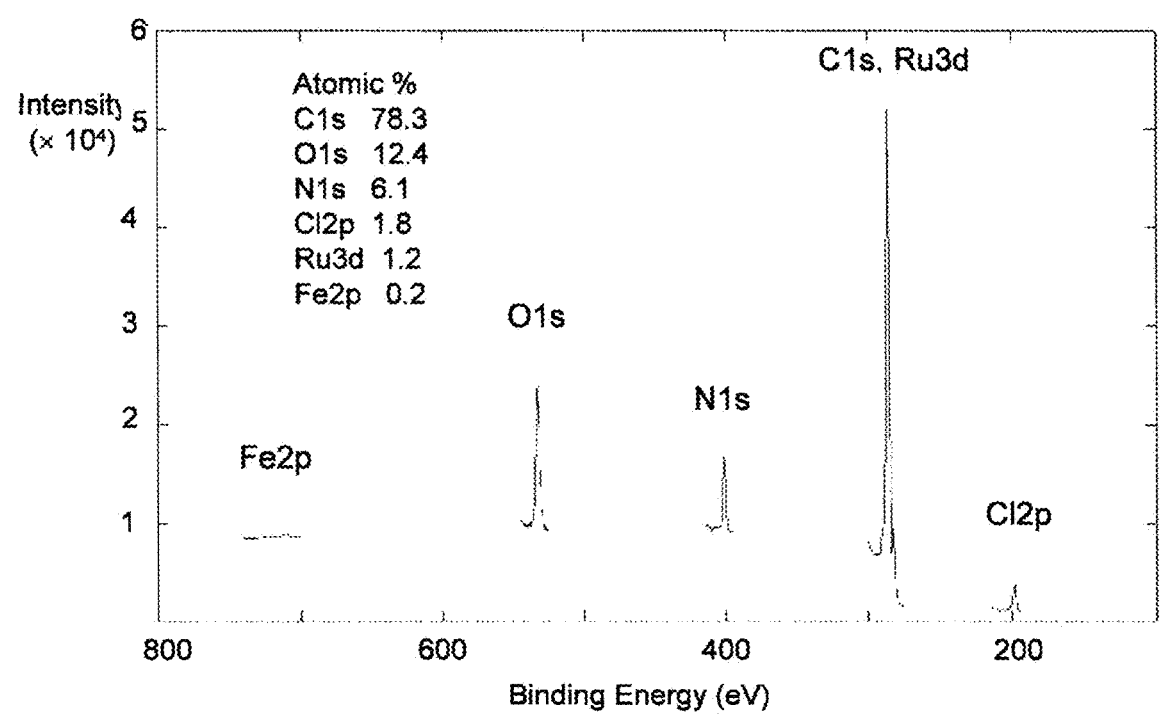
FIG. 4 shows XPS spectra of the compound of formula 6.
Figure 5:
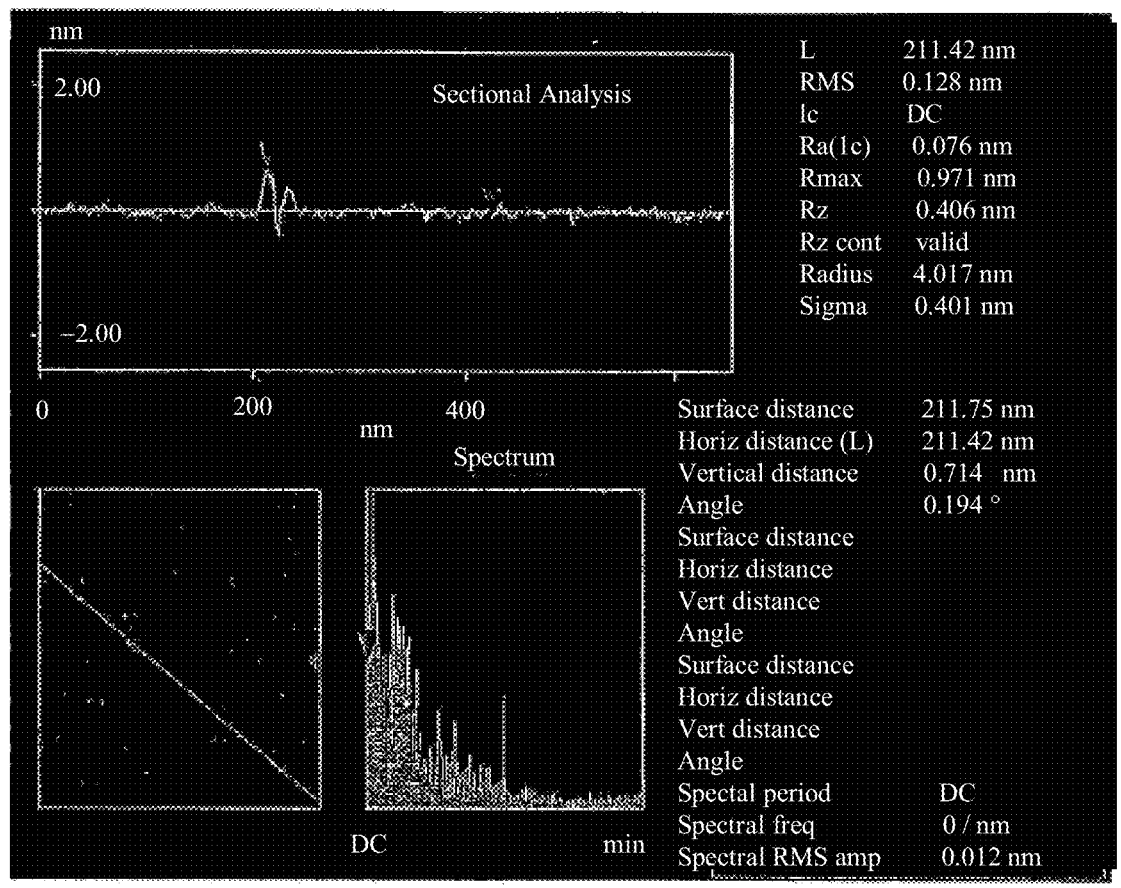
FIG. 5 shows AFM images of the compound of formula 6.

X-ray photoelectron spectroscopy (XPS, using monochromatic Mg Kα radiation at a power of 250 W) was undertaken in order to verify the presence of the coordinated metals and to gain more data in support of cyclic structure. This technique uses x-ray radiation to measure the characteristic electron binding energies of the elements and the intensity of the recorded peaks is related to elemental concentration. The XPS spectrum, shown in FIG. 4, showed binding energy peaks at 398 and 285 eV attributed to the N1s and C1s electrons of the terpyridine ligands, respectively, as well as peaks assigned to Ru (3d$^{1/2}$ at 284 eV and 3d$^{5/2}$ at 280 eV) and Fe (2p$^{1/2}$ at 706 eV and 2p$^{3/2}$ at 709 eV) thus confirming the presence of Fe and Ru complexes. The exact atomic Ru:Fe ratio of 6:1 afforded further support for the macrocyclization of monomer of formula 5.

Energy minimization calculations for the desired fractal of formula 6, performed using molecular modeling software, indicated that the predicted structure would possess a 12.3 nm diameter and 0.7 nm height; the modeled structure of fractal 6 on a mica surface possessed a slight chair-like or bent geometry rather than strict planarity. Dynamic light scattering (DLS) experiments (see supporting information) determined the average particle size of fractal 6 to be 12.5 nm, which is the intensity-averaged hydrodynamic diameter.

Because this fractal construct possesses a uniform internal repeating (polymeric) architecture that is highly symmetrical, the NMR, UV, XPS, CV, and DLS data confirm the repeat units but do not definitively establish the overall architecture of this nanoscopic hexagonal gasket; there, it was necessary to undertake single molecule imaging studies. In order to visually confirm the hexagonal structure, a droplet of an acetonitrile solution of 6 (100 μg/500 ml) was deposited on the surface of freshly cleaved mica or Au(III), dried under ambient conditions, and subjected to atomic force microscopy (AFM). This technique allows the mapping of a surface with a tip on a cantilever that results in a topographic image of a surface; the size and sharpness of the tip determines the size of the objects that can be mapped with good resolution. AFM provides data on a sample's dimensions including height. The AFM images of individual fractal constructs reveal an average diameter of 20±2 nm, relative to the ca. 4 nm radius of curvature of the silicone tip used in the AFM measurements (FIG. 3A) thereby supporting the modeled diameter of ca. 12±2 nm. The higher magnification images exhibited clear patterns in which the six ruthenium hexamers and the central hole were clearly discernible.

Figure 3:
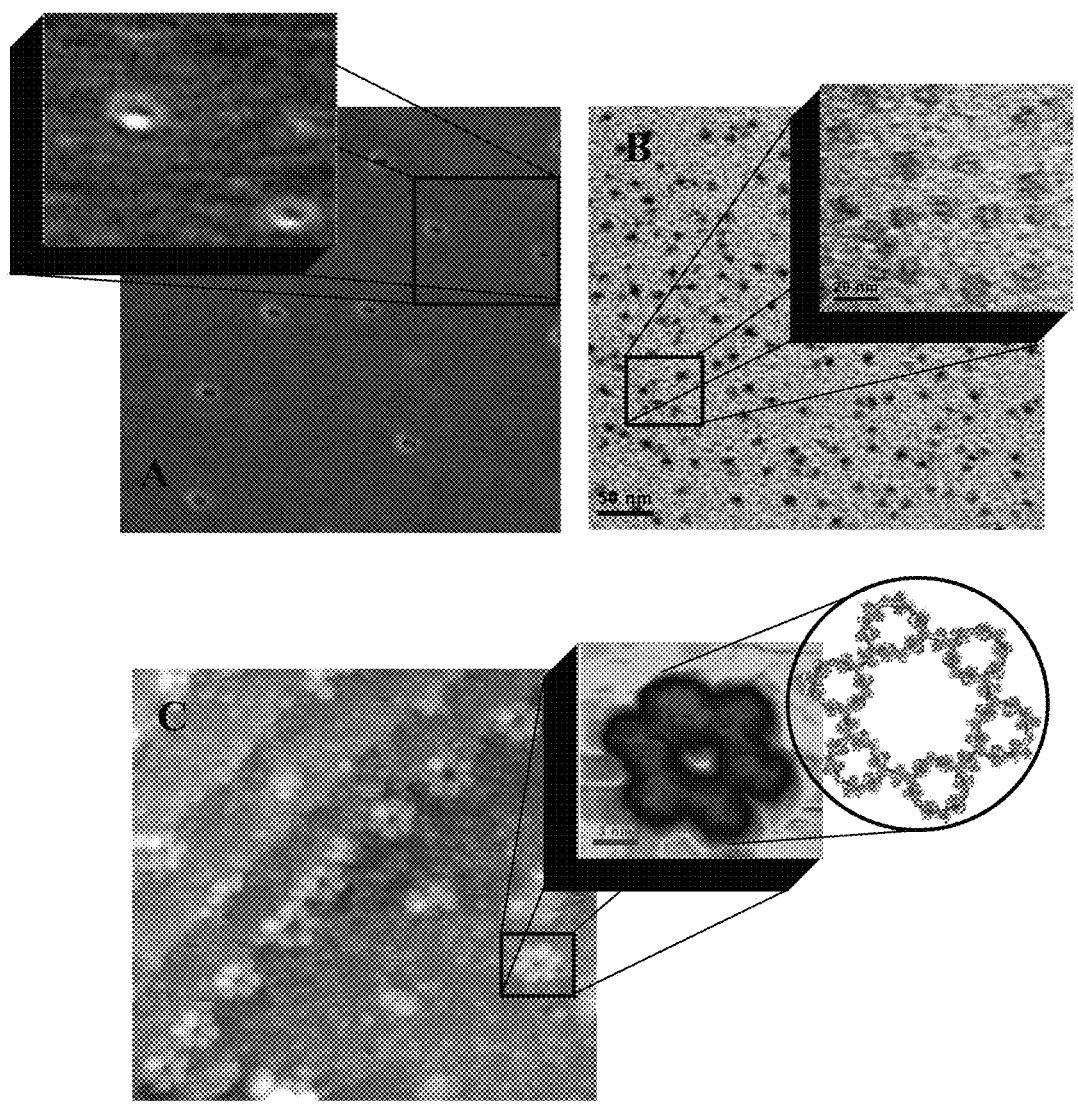
FIG. 3 shows images of gasket 6, with FIG. 3A showing AFM images at 1.12×1.12 μm and 100×100 nm.

Transmission electron microscopy (TEM; FIG. 3B) was also employed for characterization. TEM analysis provides the size, shape, and arrangement of a specimen and in some cases can provide crystallographic information. After casting a dilute methanol solution of 6 (250 μg/100 ml) on carboncoated grids (Cu and Ni, 400 mesh), the resultant analysis showed the predicted fractal-like pattern (FIG. 3B) possessing an average diameter of 11±1 nm for the single molecule, which gives direct evidence for the macrocyclization. Study of a higher magnification TEM image (FIG. 3B insert) reveals individual hexagonal gaskets lying flat or slightly tilted.

Ultra-high vacuum low-temperature scanning tunneling microscopy (UHV-LT-STM) was also employed to image the structure. This apparatus can generate images with atomic resolution by directly measuring electronic states. Ultra-high vacuum allows clean, controlled surface preparation and cryogenic temperatures to help reduce electronic noise and slow molecular motion. Using the same dilution employed for the TEM sample preparation, fractal construct 6 in acetonitrile was cast onto a freshly cleaned AU(III) surface. STM images acquired at 6 K (FIG. 3C) verified a hexagonal pattern of the molecule (12±1 nm diameter, and ca. 0.8 nm in height), which was consistent with the computer-generated model of the structure. Tunneling conductance spectra determined for single molecules at 6 K showed a 1 eV energy gap. Traces of linear oligomeric as well as larger macrocyclic assemblies were also observed on the STM images (see supporting information) and will be considered in detail elsewhere.

Experimental Section

Figure 7:
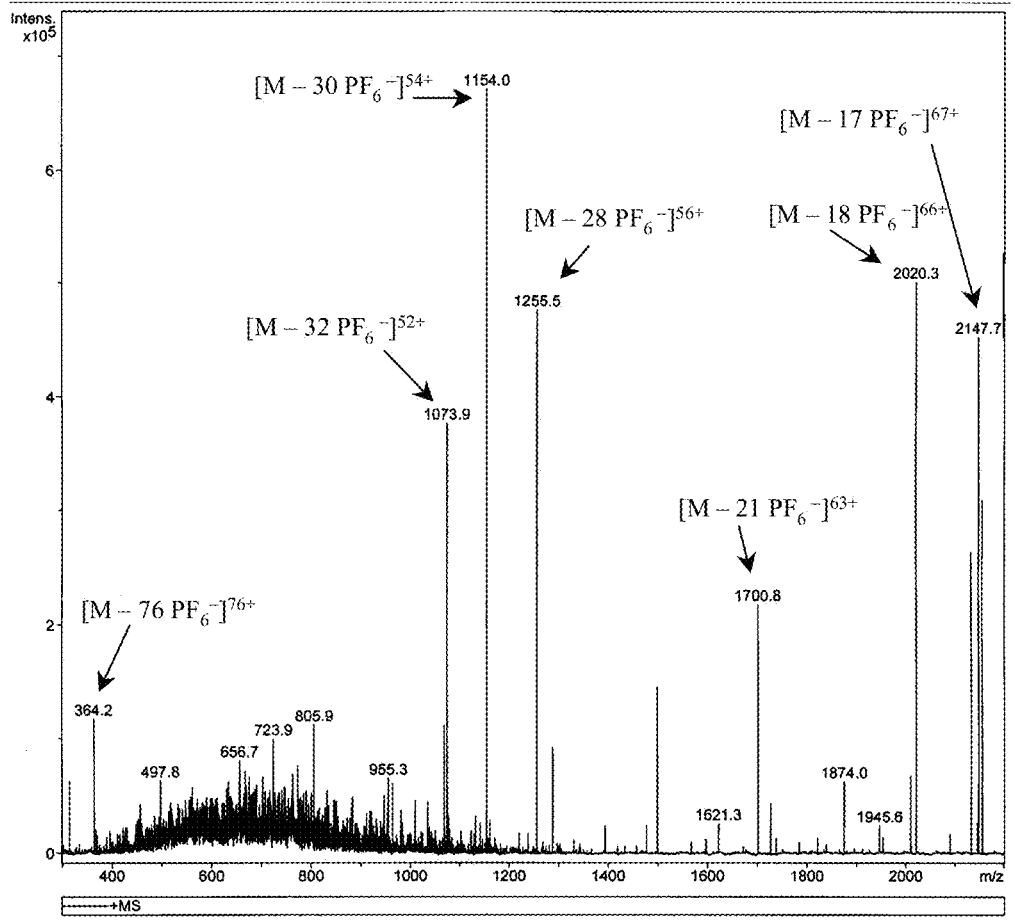
FIG. 7 shows ESI/MS of the gasket of formula 6.

The bis-Ru(III) monomer of formula 1, 1,3,5-tris(4'-terpyri-dinyl)benzene of formula 2, and bis[Ru(III),Ru(II)] trimer of formula 4 were prepared according to literature methods. Melting point data were obtained in capillary tubes with an Electrothermal 9100 melting point apparatus and are uncorrected. All other commerically available solvents were used without further purification. Column chromatography was conducted using silica gel (60-200 mesh) from Fisher Scientific and aluminium oxide (activated, basic) from Aldrich with the stipulated solvent mixture. $^1$H and $^{13}$C NMR spectra were obtained in stipulated solvent with TMS standard and are recorded on a Varian Unityplus 750 or Gemini 300. Infrared spectra (IR) were obtained (KBr pellet, unless otherwise noted) and recorded on an ATI Mattson Genesis Series FTIR spectrometer. With reference to FIG. 7, mass spectral data were obtained using an Esquire electron ionization mass spectrometer (ESI-MS) and are reported as: (assignment, relative intensity); ESI samples were typically prepared in MeOH/H$_2$O/TFA (70:30:01) for positive ion mode or Me$_2$CHOH/H$_2$O/NH$_3$ (70:30:1) for negative ion mode and matrix assisted laser desorption ionization time-of-flight (MALDI-TOF) mass spectra were obtained using a Bruker Daltonics Reflex III mass spectrometer. A transmission electron microscope (TEM, FEI TECNAI 12) with an accelerating voltage of 120 kV was used in which the samples were prepared by adding a droplet of a dilute solution onto the 400-mesh Cu or Ni grids (available from SPI Supplies), followed by drying at 25° C. for 48 hours. A scanning probe microscope (Digital Instruments Nanoscope IIIa) equipped with a Multi 75, Force Modulation Etched Silicon Probe (MPP-21100) was utilized operating in tapping mode (AFM); a droplet of a dilute solution was place on the surface of freshly cleaved mica or Au(III), then dried at 25° C. for 6 hours. UV-Vis spectra were recorded on a Ocean Optics, Inc. Chem2000 UV-Vis spectrophotometer. Electrochemical measurements (cyclic voltammetry) were performed on a potentiostat (CH Instruments Inc. CHI-4401) at 25° C. using a three-electrode configuration cell: a mini-glassy carbon electrode (CHI, 2 mm dia.) for the working electrode, platinum wire for the counter electrode, and Ag/AgNO$_3$ for the reference electrode. Ferrocene was added at the end of the experiment as an internal standard; all potentials were measured relative to the Fc/Fc$^+$ couple. Solutions were stirred and degassed with argon prior to each voltammetric measurement. The dynamic light scattering (DLS) measurement was performed using a Brookhaven BI-200SM system operating at wavelength of 632.8 nm at 25.0° C. with a fixed scattering angle of 90°. A Brookhaven BI-9000AT digital autocorrelator was used to compute the scattered photons time autocorrelation function, which was analyzed by a cumulants method to determine both the average particle size and polydispersity. Ultrahigh vacuum, low temperature, scanning tunneling microscopy (UHV-LT-STM) experiments were performed at 6 K substrate temperature by using a home-built system with a Besoke-Beetle type STM scanner. The Au (III) sample was cleaned by repeated cycles of sputtering and annealing up to 1000 K. An electrochemically etched polycrystalline tungsten wire was used for the STM tip. The tip apex is prepared by using a controlled tip-crash procedure. The fractal gasket 6 was deposited onto the cleaned Au (III) surface at 25° C., and then cooled to 6 K inside the STM system.

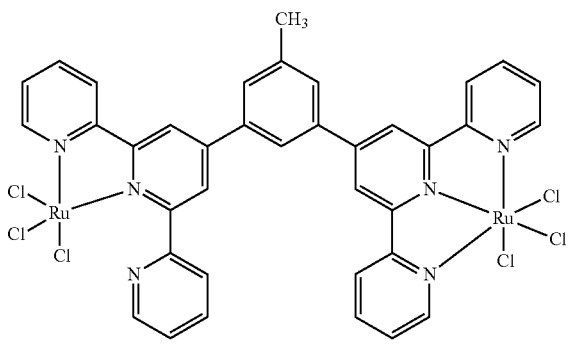

1

-continued

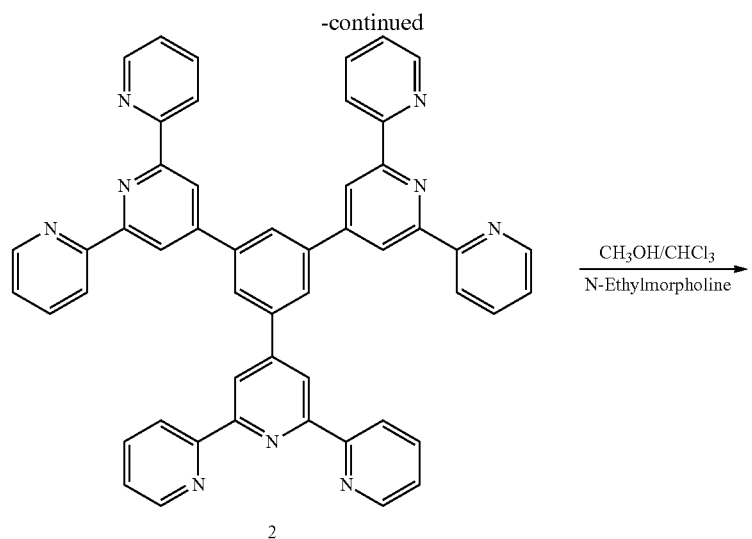

2

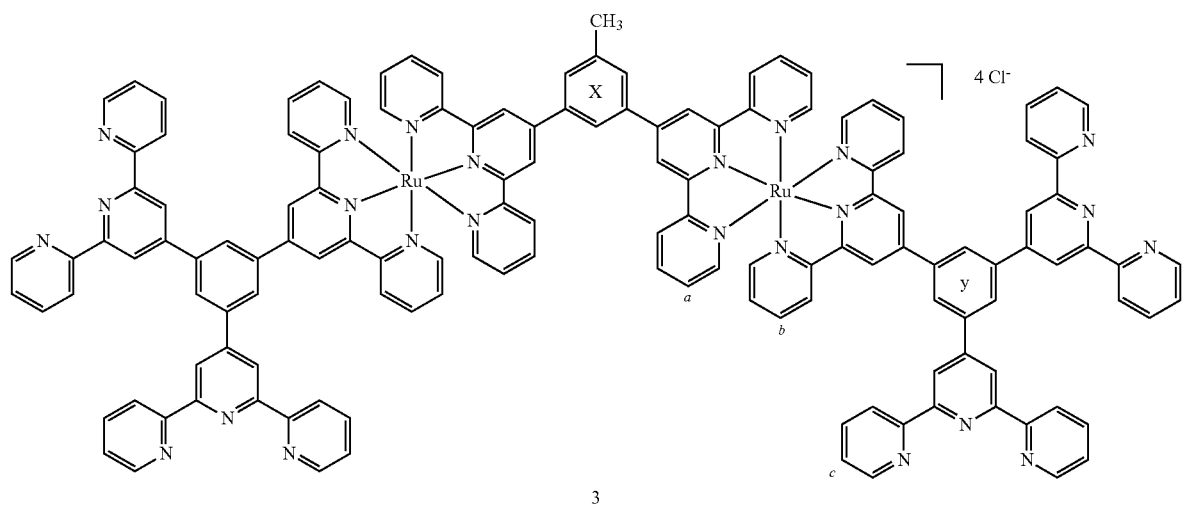

3

Syntheses of Bis[Ru(II)]-dimer of formula 3, Tristerpyridine (formula 2) (150 mg, 194 µmol) was dissolved in CHCl$_3$ (10 mL), followed by the addition of MeOh (15 mL), then the mixture was refluxed for 2 hours. Solid bis[Ru(III)]-dimer (formula 1) (mp>400° C. lit. mp>400° C.; 78 mg, 80 µmol) was added; the mixture was refluxed for an additional hour, then 5 drops of N-ethylmorpholine was added. The stirred solution was refluxed for 12 hours, cooled, filtered through a celite layer; the resultant red solution was concentrated in vacuo to give a red powder, which was dissolved in CHCl$_3$ and column chromatographed through a short column of Al$_2$O$_3$ eluting first with CHCl$_3$ to remove excess of the starting material of formula 2 then adjusting the elution solvent to H$_2$O/MeCN/KNO$_3$ (1:7:1) afforded (35%, 68 mg), after the addition of NH$_4$PF$_6$, the desired bis[Ru(II)]-tetrakisligand of formula 3, as red microcrystals: mp>300° C.; $^1$H NMR (CD$_3$CN): δ 2.86 (s, 3H, CH$_3$), 7.21 (t, 4H, 5,5"-$^b$PyH, J=6.6 Hz), 7.35 (t, 4H, 5,5"-$^a$PyH, J=6.0 Hz), 7.48 (t, 8H, 5,5"-$^c$PyH, J=6.3 Hz), 7.49 (d, 4H, 6,6"-$^b$PyH, J=5.1 Hz), 7.54 (d, 4H, 6,6"-$^a$PyH, J=5.1 Hz), 7.92 (m, 16H, 4,4"-$^{a,b,c}$PyH), 8.06 (s, 2H, $^y$ArH), 8.33 (s, 2H, $^y$ArH), 8.50 (s, 2H, $^y$ArH), 8.61 (s, 4H, $^x$ArH), 8.63 (d, 8H, 3,3"-$^c$pyH, J=7.2 Hz), 8.72 (d, 8H, 6,6"-$^c$pyH, J=4.2 Hz), 8.84 (m, 8H, 3,3"-$^{a,b}$tpyH), 9.05 (s, 8H, 3',5'-$^c$tpyH), 9.12 (s, 4H, 3',5'-$^b$pyH), 9.26 (s, 4H, 3',5'-$^a$pyH); ESI-MS (2880.38; C$_{139}$H$_{92}$F$_{24}$N$_{24}$P$_4$Ru$_2$): m/z: 2736.6 M-PF$_6$)$^+$, 1295.9 (M-2PF$_6$)$^{2+}$.

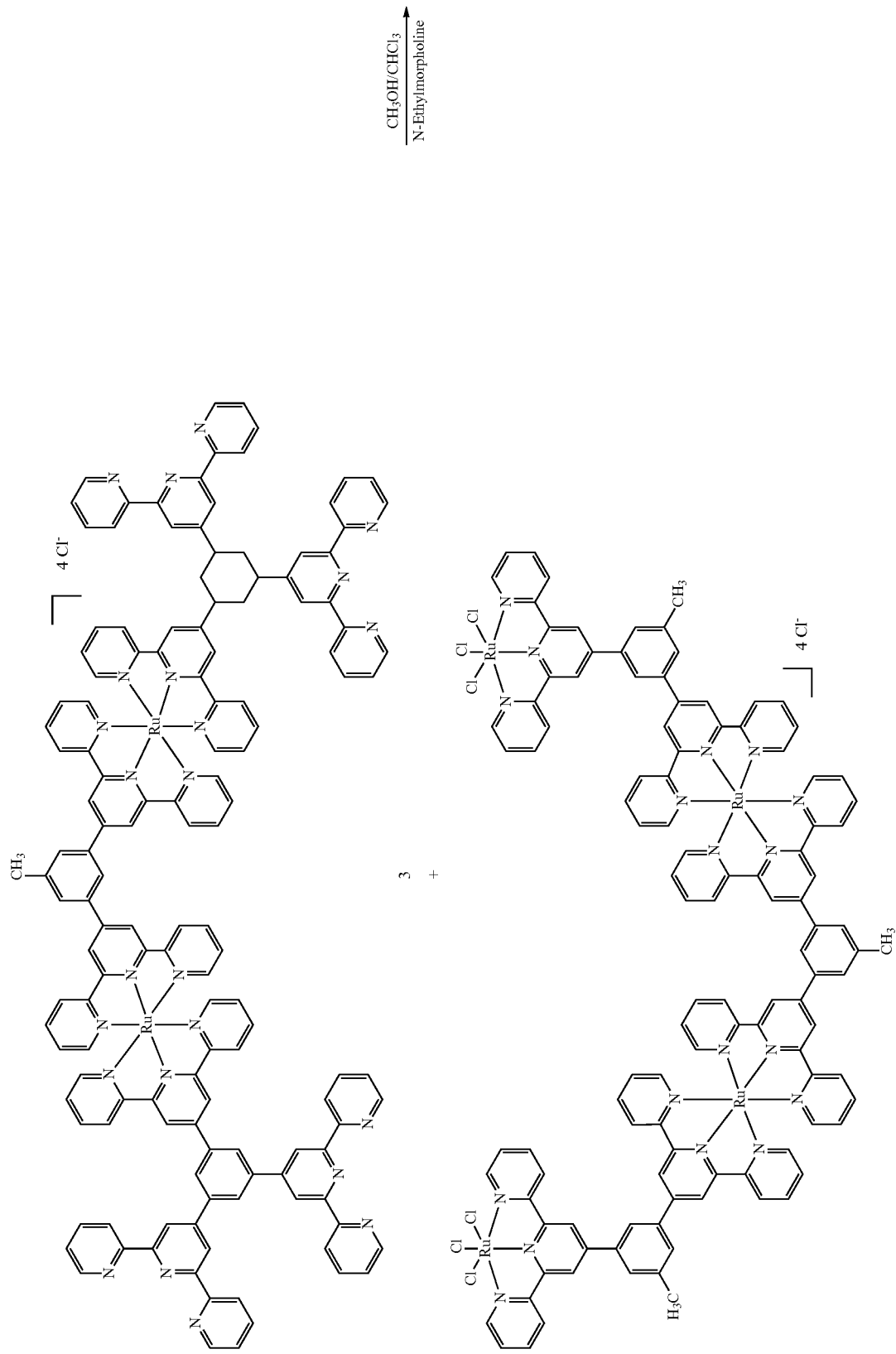

-continued
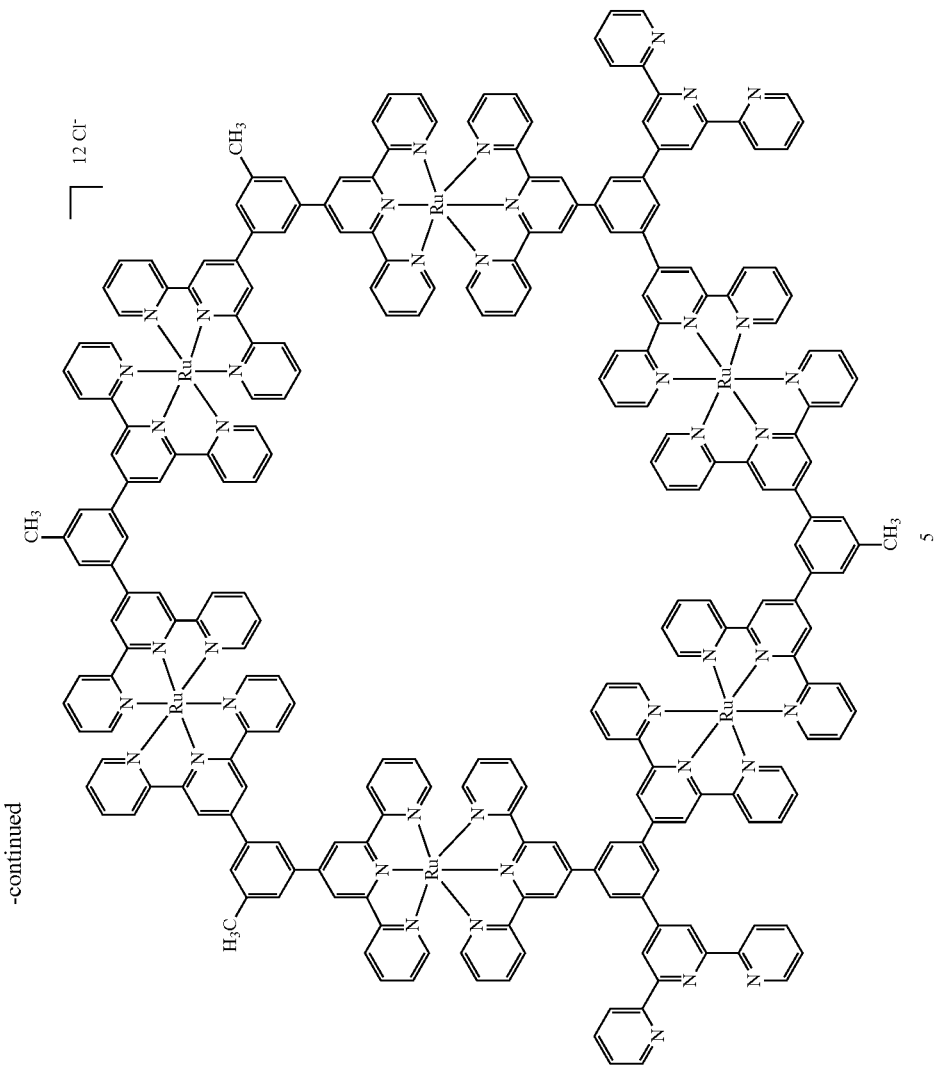

Synthesis of Hexa[Ru(II)]-bis-ligand of Formula 5

A suspension of bis[Ru(III)Ru(II)]-complex of formula 4 [mp>400° C. (lit.[1] mp>400° C.), 75 mg, 31.0 µmol] and the tetrakisligand of formula 3 (75.6 mg; 31.0 µmol) in MeOH (70 mL) was refluxed for 2 hours, then 5 drops of N-ethylmorpholine was added. The mixture was refluxed for an additional 12 hours; the clear red solution was precipitated from a MeOH/hexane mixture to give as a red solid, which was dissolved in MeOH and column chromatographed ($Al_2O_3$) eluting with a $H_2O$/MeCN/$KNO_3$ (1:7:1) solution to afford (31%, 47 mg) hexameric bis-ligand of formula 5, as a microcrystals: mp>300° C.; $^1$H NMR ($CD_3CN$): δ 2.86 (s, 12H, $CH_3$), 7.25 (m, 24H, 5,5"-tpyH), 7.52 (m, 16H, 6,6"-tpyH), 8.00 (m, 24H, 4,4"-tpyH), 8.33 (m, 12H, ArH), 8.79-8.73 (m, 32H, 3,3"-tpyH+ArH), 9.18 (s, 4H, free 3',5'-tpyH), 9.23 and 9.24 (m, 24H, 3',5'-tpyH); ESI-MS (6108.30; $C_{250}H_{170}F_{72}N_{42}P_{12}Ru_6$); m/z: 1077.8 (M-5 $PF_6$)$^{5+}$, 874.2 (M-6 $PF_6$)$^{6+}$, 727.7 (M-7 $PF_6$)$^{7+}$, 618.3 (M-8 $PF_6$)$^{8+}$, 533.8 (M-9 $PF_6$)$^{9+}$, 465.8 (M-10 $PF_6$)$^{10+}$, 410.4 (M-11 $PF_6$)$^{11+}$, 364.2 (M-12 $PF_6$)$^{12+}$.

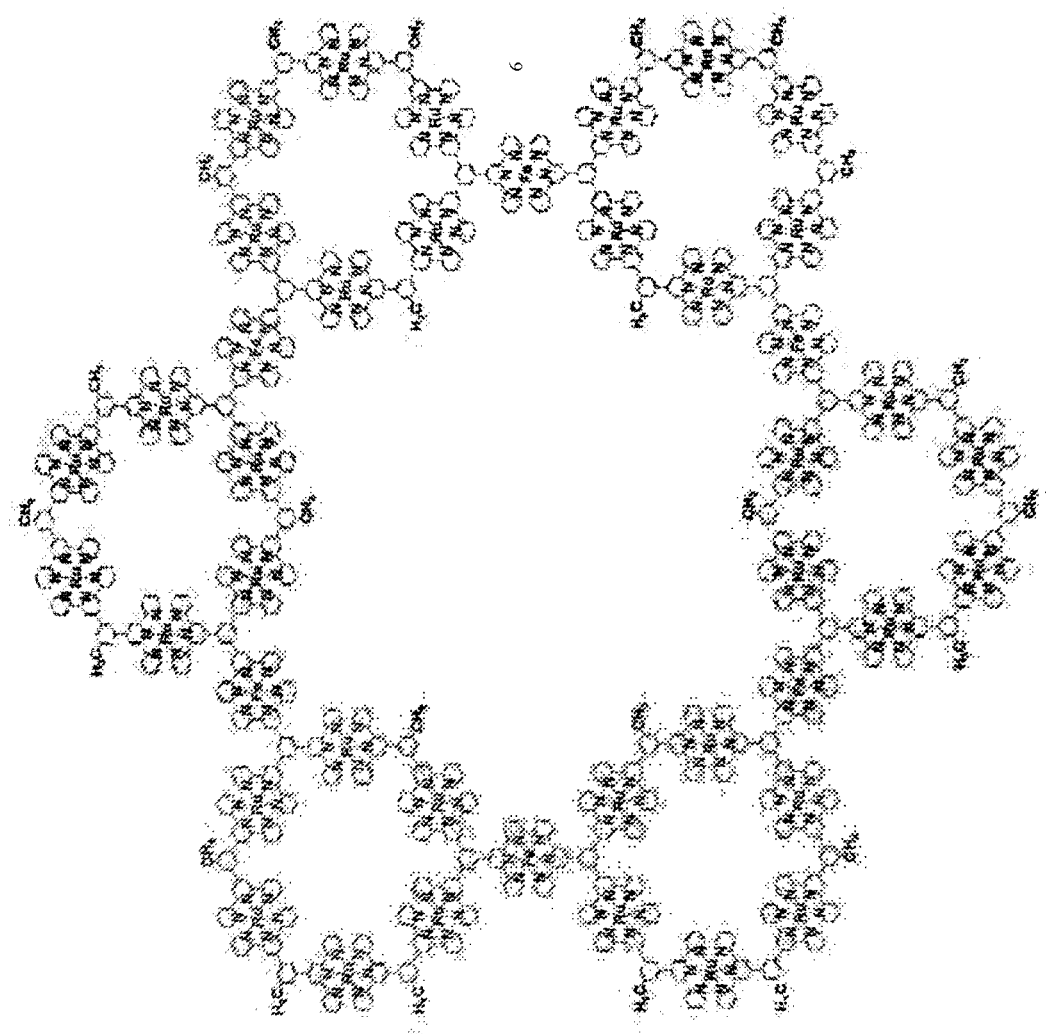

Synthesis of the Fractal Gasket of Formula 6.

A mixture of the bis-ligand of formula 5 (30 mg, 6 µmol) and 1 equiv. of $FeCl_2$ (1.5 mg) in MeOH (60 mL) was refluxed for 12 hours to give a deep red solution, which was filtered through celite, concentrated in vacuo and dialyzed (MWCO: 8000) with MeOH for 3 days (replacing the outside solvent until colorless) and then column chromatographed ($SiO_2$) eluting with a $H_2O/MeCN/KNO_3$ (1:7:1) solution. After washing with water, the red microcrystalline was dissolved in $CH_3OH$. The internal red solution was treated with excess of methanolic $NH_4PF_6$ to generate a red precipitate, which was filtered, washed with MeOH (3×5 mL), then dissolved in $CH_3CN$ (10 ml), and reprecipitated by adding hexane (ca. 25 ml) to give (35%, 14 mg) the desired fractal of formula 6, as red microcrystals: mp>300° C.; $^1H$ NMR ($CD_3CN$) δ 2.86 (s, 12H, $CH_3$), 7.27 (m, 28H, Fe-5,5"-typH+5,5"-tpyH), 7.57 (m, 24H, Ru-6,6"-tpyH), 7.68 (b, 4H, Fe-6,6"-tpyH), 8.02 (m, 28H, Fe-4,4"-tpyH+Ru-4,4"-tpyH), 8.38 (m, 8H, ArH), 8.87 (m, 10H, ArH), 8.91 (m, 24H, Ru-3,3"-tpyH), 9.14 (b, 4H, Fe-3,3"-tpyH), 9.39 (m, 24H, Ru-3', 5'-tpyH), 9.79 (b, 4H, Fe-3',5'-tpyH); $^{13}C$ NMR ($CD_3OD$) δ 22.05, 134.58, 124.36, 126.67, 129.20, 131.70, 139.79, 142.65, 149.89, 153.36, 157.18, 157.50, 159.91, 162.13; UV/Vis (MeCN): $\lambda_{max}$=290 (tpy), 495 (tpy-Ru-tpy), 575 $cm^{-1}$ (tpy-Fe-tpy); ESI-MS showed the broad peaks range from m/z at 310 to 970 attributed to multi-charged stages ($35^+$ to $84^+$).

Molecular modeling was performed using version 4.7 Cerius2 software available from Accelyrs. The $C^2$ Visualizer module was used to build the molecule that was minimized using the Smart Minimizer with the standard convergence criteria (i.e., atomic root mean square force 0.100 kcal/mol, overall energy difference $1.00 \times 10^{-3}$ kcal/mol, and an overall root mean square displacement $3,000 \times 10^{-3}$).

Figure 6:
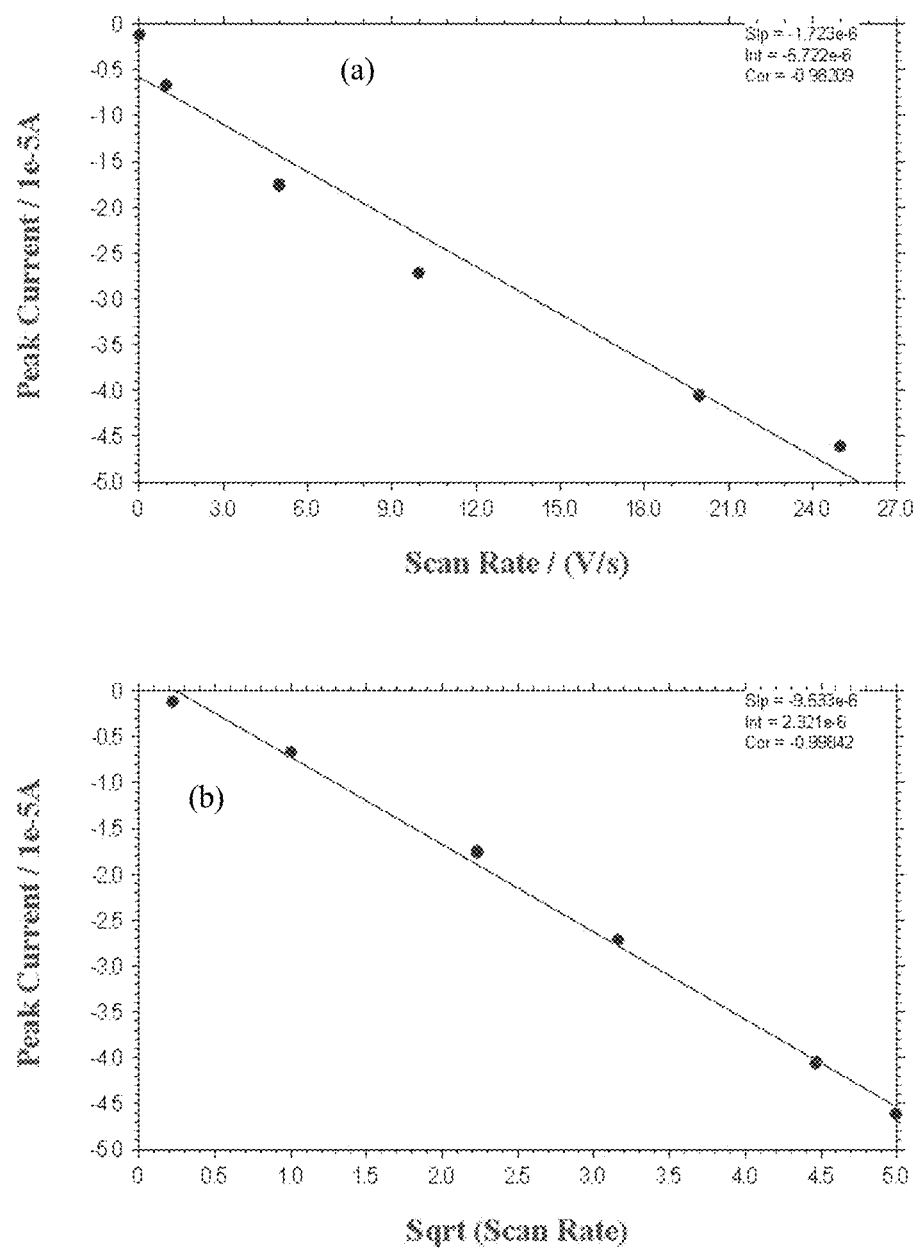
FIG. 6, shows a plot of peak current vs. scan rate in (a) and vs. the square root of scan rate (b) taken from cyclic voltammetric data for fractal of formula 6.

The fractal of formula 6 appears to be diffusion controlled, rather than absorptive; this can be readily demonstrated with plots of the dependence of peak current with scan rate (FIG. 6A), in which peak current grows proportionally to the square root of the scan rate (FIG. 6B).

What is claimed is:

1. A macromolecule comprising: a non-dendritic, fractal construct including:
    terpyridine building blocks with terpyridine groups bound through coordination to form a first generation structure, said first generation structures having terpyridine groups;
    a second generation structure comprising said first generation structures bound through coordination at the terpyridine groups thereof, said second generation structures having terpyridine groups; and
    a third generation structure comprising said second generation
    structures bound through coordination at the terpyridine groups thereof;
wherein the macromolecule has an outer surface area, and the macromolecule includes functionalization located on the outer surface area.

2. The macromolecule of claim 1, where the terpyridine group coordination includes terpyridine groups coordinated to an iron ion.

3. The macromolecule of claim 1, where the terpyridine group coordination includes terpyridine groups coordinated to a ruthenium ion.

4. The macromolecule of claim 1, where the terpyridine group coordination includes terpyridine groups coordinated to a zinc ion.

5. The macromolecule of claim 1, where the terpyridine building blocks include bis-terpyridine building blocks.

6. The macromolecule of claim 1, where the terpyridine building blocks include tris-terpyridine building blocks.

7. The macromolecule of claim 1, where the functionalization provides hydrophobic character.

8. The macromolecule of claim 1, where the functionalization provides hydrophilic character.

9. The macromolecule of claim 1, where the macromolecule has an inner surface area, and the macromolecule includes functionalization located on the inner surface area.

10. A molecular battery comprising the macromolecule of claim 1.

11. A method of assembling a fractal construct, the method comprising the steps of:
    coordinating functionalized bis-terpyridine building blocks with tris-terpyridine building blocks to form heterotrimers, wherein the functionalized bis-terpyridine building blocks have hydrophobic character;
    coordinating bis-terpyridine building blocks to form homotrimers;
    coordinating the heterotrimers with the homotrimers to form hexamers; and
    coordinating the hexamers to form a fractal gasket.

12. The method of claim 11, where a functionalized bis-terpyridine building block is coordinated with tris-terpyridine building blocks to form the heterotrimers.

13. The method of claim 11, where a functionalized bis-terpyridine building block is coordinated form the homotrimers.

14. A macromolecule comprising: a non-dendritic, fractal construct including:
    terpyridine building blocks with terpyridine groups bound through coordination to form a first generation structure, said first generation structures having terpyridine groups;
    a second generation structure comprising said first generation structures bound through coordination at the terpyridine groups thereof, said second generation structures having terpyridine groups; and
    a third generation structure comprising said second generation structures bound through coordination at the terpyridine groups thereof;
    wherein the macromolecule has an inner surface area, and the macromolecule includes functionalization located on the inner surface area.

15. The macromolecule of claim 14, where the terpyridine group coordination includes terpyridine groups coordinated to an iron ion.

16. The macromolecule of claim 14, where the terpyridine group coordination includes terpyridine groups coordinated to a ruthenium ion.

17. The macromolecule of claim 14, where the terpyridine group coordination includes terpyridine groups coordinated to a zinc ion.

18. The macromolecule of claim 14, where the terpyridine building blocks include bis-terpyridine building blocks.

19. The macromolecule of claim 14, where the terpyridine building blocks include tris-terpyridine building blocks.

20. The macromolecule of claim 14, where the functionalization provides hydrophobic character.

21. The macromolecule of claim 14, where the functionalization provides hydrophilic character.

22. The macromolecule of claim 14, where the macromolecule has an outer surface area, and the macromolecule includes functionalization located on the outer surface area.

23. A molecular battery comprising the macromolecule of claim 1.

24. A method of assembling a fractal construct, the method comprising the steps of:
- coordinating functionalized bis-terpyridine building blocks with tris-terpyridine building blocks to form heterotrimers, wherein the functionalized bis-terpyridine building blocks have hydrophilic character;
- coordinating bis-terpyridine building blocks to form homotrimers;
- coordinating the heterotrimers with the homotrimers to form hexamers; and
- coordinating the hexamers to form a fractal gasket.

25. The method of claim 24, where a functionalized bis-terpyridine building block is coordinated with tris-terpyridine building blocks to form the heterotrimers.

26. The method of claim 24, where a functionalized bis-terpyridine building block is coordinated form the homotrimers.

* * * * *